US012551363B2

(12) United States Patent
Gorup Valenzuela et al.

(10) Patent No.: US 12,551,363 B2
(45) Date of Patent: Feb. 17, 2026

(54) HAND-AND-WRIST ACCESSORY DEVICE FOR PEOPLE THAT FACILITATES EXTENSION MOVEMENTS

(71) Applicant: GOGO LABS SPA, Las Condes Santiago (CL)

(72) Inventors: Cristian Eduardo Gorup Valenzuela, Las Condes Santiago (CL); Diego Antonio Godoy Santander, Maipú Santiago (CL)

(73) Assignee: GOGO LABS SPA, Las Condes Santiago (CL)

( * ) Notice: Subject to any disclaimer, the term of this patent is extended or adjusted under 35 U.S.C. 154(b) by 224 days.

(21) Appl. No.: 18/250,872

(22) PCT Filed: Oct. 18, 2021

(86) PCT No.: PCT/CL2021/050103
§ 371 (c)(1),
(2) Date: Apr. 27, 2023

(87) PCT Pub. No.: WO2022/094736
PCT Pub. Date: May 12, 2022

(65) Prior Publication Data
US 2023/0398012 A1 Dec. 14, 2023

(30) Foreign Application Priority Data
Nov. 4, 2020 (CL) .................................. 2852-2020

(51) Int. Cl.
*A61F 5/01* (2006.01)

(52) U.S. Cl.
CPC .................................. *A61F 5/013* (2013.01)

(58) Field of Classification Search
CPC .......... A61F 5/013; A61F 5/0118; A61F 5/05; A61F 5/05866; A61F 5/05875;
(Continued)

(56) References Cited

U.S. PATENT DOCUMENTS 8,491,447 B1 * 7/2013 Koranic ................ A63B 23/16
482/44
2006/0211964 A1 * 9/2006 Farrell ................. A61F 5/0118
602/5

(Continued)

*Primary Examiner* — Adam Baker
(74) *Attorney, Agent, or Firm* — Gottlieb, Rackman & Reisman, PC

(57) ABSTRACT

Disclosed is a hand-and-wrist accessory device formed by an elasticated glove, wherein the ends of the fingers and the end of the wrist comprise an internal elasticated silicone layer that acts as a mechanical securing element for securing to the skin, these securing elements being connected to rigid structures connected to elastic elements, transmitting elastic energy from the wrist to a central floating piece on the dorsal carpus, where it is distributed to each finger terminal, the elastic elements being guided by rigid pieces disposed in the paths extending from the central piece to the finger terminals, to ensure the correct alignment thereof. These external elements have reciprocal securing elements to generate continuity from the wrist terminal to the finger or digit terminals. Cushioned elements are disposed on the palm to redistribute pressure in the wrist areas.

6 Claims, 5 Drawing Sheets

(58) Field of Classification Search
CPC .. A61F 5/10; A61F 5/3723; A61F 5/42; A61F 2005/0146; A61F 2005/0165; A61F 2005/0169; A61F 2005/0179; A61F 2005/197; A41D 13/08–088; A63B 71/14–148; A63B 21/4025; A63B 21/4019; A63B 21/0552; A63B 21/0555; A63B 21/0557; A63B 23/16; A61H 1/0288
USPC .......................................................... 602/21
See application file for complete search history.

(56) References Cited

U.S. PATENT DOCUMENTS

2010/0234182 A1* 9/2010 Hoffman ................. A61F 5/013 482/8
2012/0059298 A1* 3/2012 Hoffman ................. A61F 5/013 602/21
2014/0257159 A1* 9/2014 Kelly .................... A61F 5/0118 602/21

* cited by examiner

HAND-AND-WRIST ACCESSORY DEVICE FOR PEOPLE THAT FACILITATES EXTENSION MOVEMENTS

FIELD OF THE INVENTION

The present application relates to a (dynamic) orthotic glove that facilitates finger and wrist extension movements in typing, this accessory specifically performing the function of preventing painful symptoms in the hand and wrist by means of padded elastic structures with the function of reducing fatigue and damage to extensor muscles of the fingers, hand and wrist by redistributing pressures at anatomical points such as the carpal tunnel, hypothenar, and thenar of the hand.

BACKGROUND

At present, injuries due to repetitive movements are common in typing and manufacturing professions. With the massification of technology, these pathologies and symptoms have shown an increase across age and gender, and additionally there is a variable use of repetitive movements in leisure time that increases the possibility of generating pathologies such as carpal tunnel, tendinitis, trigger finger, and tenosynovitis.

Conventional therapies for these complications are immobilization by orthotics, neuromuscular taping, pharmacotherapy, and kinesiological or physiotherapeutic rehabilitation when an acute or chronic pathological phenomenon has been diagnosed, and in some cases, a surgical solution is reached. The prevention of these injuries is achieved by means of periodic stretching of the hand and wrist muscles, and ergonomic postures and accessories.

One of the therapeutic principles of neuromuscular taping is the mechanical facilitation of muscles by means of elastic bands that are positioned on the path of a muscle or set of muscles related to the action movement produced by them.

There are several hand and upper limb accessories to protect these structures from different variables, from temperature to extreme mechanical forces. There are also those serving ornamental and comfort purposes, on the other hand, there are orthotics for the treatment of hand, wrist and forearm pathologies which are designed for the treatment of such pathologies and prevent their recurrence in response to a diagnosis, maintaining a principle of graduated restricted mobilization and/or immobilization of the anatomical structures so that these comply with the healing process without further complexity.

One of the most representative solutions in typing work environments is to follow ergonomic standards that are designed to avoid health complications of this type, with workstations generally having accessories for the purposes of preventing and protecting against hand, wrist and forearm injuries due to repetitive movements and poor postures. Even so, these interventions are not entirely effective because they are passive, are not integrated into a single device for routine use and are dependent on the participation of the users.

The methods mentioned and currently used have the additional drawback of being primarily solutions in response to a diagnosis or advanced stage of deterioration, and those that are for prevention are by means of passive elements, requiring guidance and monitoring by a professional, reducing the effectiveness of the therapeutic objective and affordability of techniques for prevention.

It is therefore apparent that there is a need for an element that performs the prevention of painful symptoms in repetitive typing work that is independent of the installation, guidance, and monitoring of a professional on site, with structures that are dynamic with respect to the movement of the hand and passive at pressure points, protecting the anatomical structures related to tendon pathologies and nerve compression.

Among the patents investigated, the most similar is patent US2005/223469A1, also for prevention with respect to repetitive movements, the difference with the present invention being that this patent focuses on bending movements and on console type video game controls, its principle being the use of terminal agents for the protection of muscles and mechanical facilitation.

The solution proposed in the present application is based on the objective of facilitating movement and reducing the mechanical loading of finger extension, resembling the widely used therapeutic principle of neuromuscular taping (USPTO no. 3523859) and selectively protecting pressure areas by means of passive cushioned elements, ensuring the protection of the anatomical structures related to tendon and nerve pathologies.

In this context, the incorporation of this accessory, which may comply with the therapeutic objectives of prevention independent of the installation, guidance and correction of a healthcare professional, is vital for increasing the affordability of elements for prevention in typing work and opens up a new concept for different areas of work using repetitive hand movements, protecting the health of workers and preventing restrictions on their daily life activities.

DESCRIPTION OF THE INVENTION

The accessory consists of a glove with cut out fingers which, in the upper part, has elastic external structures that exert mechanical support on the path of the tendons of the common extensor muscle of the fingers for the purpose of facilitating the extension of fingers from the flexed finger position when typing on keys, in addition to cushioned structures on the thenar areas, hypothenar areas, pads, radius and ulnar areas, in the terminal areas of the fingers and wrist, is secured to the skin by means of silicone fabric on the inside of the glove, for the purpose of providing external structures with a mechanical securing element required for facilitating extension movements.

The glove is formed by breathable, hypoallergenic, elastane (spandex), non-toxic, washable, anti-fungal silicone microfibers in the distal areas of the fingers and wrist, being of a single color, of various colors or textures, shapes, and motifs, where summer or winter fabrics are also used as well.

The advantages of this accessory reside in the accessibility and ease of use of a tool for prevention without the need for installations and professional guidance, increasing comfort while at the same time releasing a load from anatomical structures, with a service life that is longer than that of neuromuscular taping, being adaptable to an elastic load, and having pieces that are easy to replace, being a reusable orthotic for the prevention of tendon pathologies, thereby preventing occupational desertion.

Considering what has been set out above, it would be beneficial to develop an accessory for alleviating or reducing the painful symptoms associated with the mechanical loading of the extensor muscles and tendons of the hand in typing positions for prolonged periods of time, performing the function of preventing muscle and tendon pathologies.

In summary, the present invention implements a glove, with elastic structures along the path of the extensor tendons (dorsal part of the hand) of the fingers, hand, and wrist, pressure dissipation structures on the thenar, hypothenar, carpal tunnel and metacarpal areas.

DETAILED DESCRIPTION OF THE INVENTION

Figure 1:
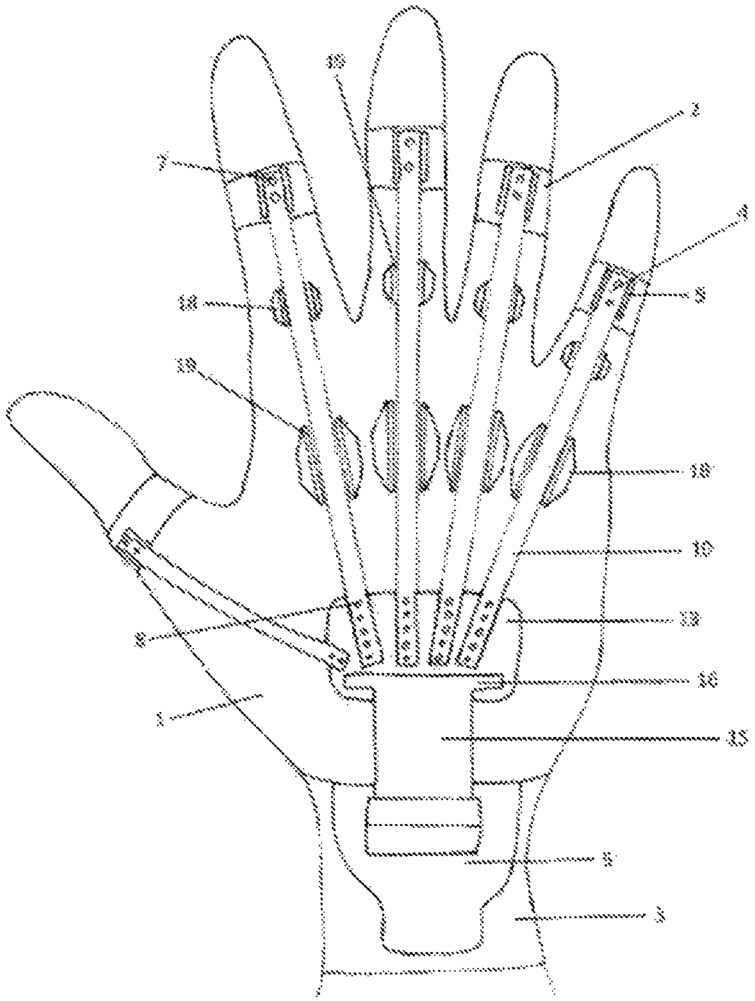
FIG. 1 is an illustration showing a hand with the glove of the present invention in a top view.
Figure 2:
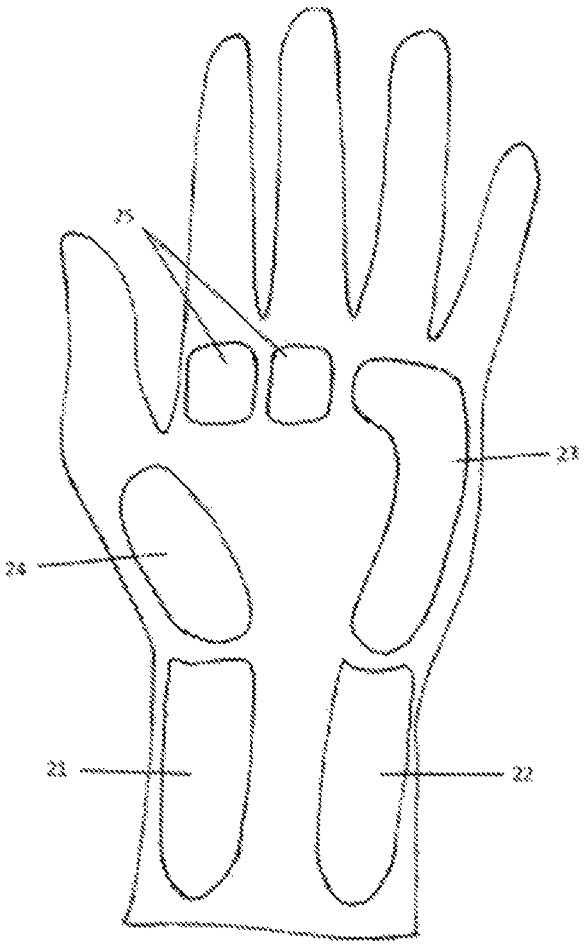
FIG. 2 is an illustration showing a hand with the glove of the present invention in a bottom or palmar view.
Figure 3:
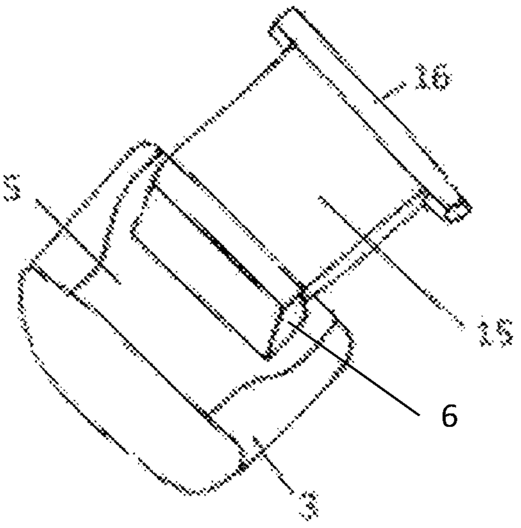
FIG. 3 depicts a top perspective view of the support and wrist securing element of the glove.
Figure 4:
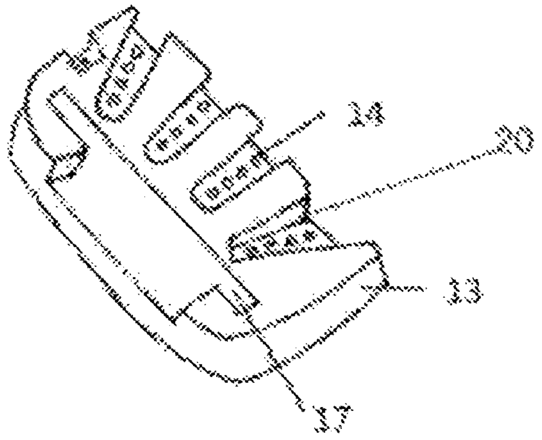
FIG. 4 depicts a top perspective view of the carpal or central securing piece of the present invention.
Figure 5:
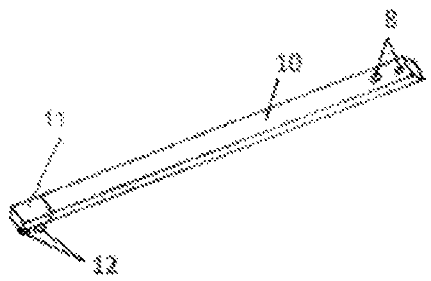
FIG. 5 depicts a top perspective view of the elastic element and the securing mechanisms of the finger and carpal tendon support system.
Figure 6:
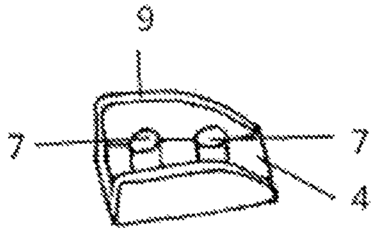
FIG. 6 depicts a top perspective view of the securing mechanisms of the distal finger tendon support system.
Figure 7:
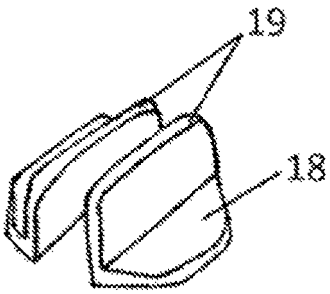
FIG. 7 depicts a top perspective view of the guide element for guiding the elastic elements along the extension path.

The (dynamic) orthotic glove that facilitates finger extension in typing work is made up of a fitted elasticated glove (1) that covers from the proximal phalanges of the thumb and medial phalanges of the fingers to the wrist joint, constituting the main body of the device where the other functional elements are housed.

The elasticated glove (1) is formed by breathable, hypoallergenic, spandex, non-toxic, washable, anti-fungal silicone microfibers in the distal areas of the fingers and wrist for the purpose securing to the skin of the hand and wrist by adhesion and compression, there being positioned in these areas rigid finger terminals (4) and a wrist terminal (15), in a wrist securing area (5) and finger securing area (2).

The rigid finger terminal (4) has two side tabs (9) for the purpose of centering the path of elastic elements (10) and has two finger connection bosses (7) which reciprocally work with elastic perforations (8) in the elastic elements (10), the elastic perforations (8) of the exotendon elastic elements (10) performing the function of generating a finger extending force when the hand is in a flexed position over a mouse or an analog computer keyboard, where the proximal part of this element has a connection terminal (11) having two extruded elastic bosses (12) which reciprocally connect with two central piece perforations (14) of a central piece (13) for the purpose of being mechanically secured and generating a tension graduation system depending on the selection of coupling points, generating a connectivity with the elastic structures disposed from the wrist securing element (5) to the rigid finger terminals (4), being attached in the central piece (13) on the dorsal part of the hand, said central piece (13) defining five slots (20) each with at least two central piece perforations (14).

The wrist securing element (5) has a certain height (6) from its securing point with the terminals for the elastic elements (10) and a joining piece (15) for the purpose of preventing friction between the aforementioned elastic pieces and the textile material of the glove.

The objective of the wrist securing element (5) adhered on the surface of the wrist (3) which internally comprises silicone is to project the joining piece (15) from an removable articulation to the central piece (13) in the area of the carpus of the glove of the hand, being secured to same by means of the articulation comprising a male articulation piece (16) with a shape extending onto a female articulation piece (17) designed to be reciprocally coupled and thereby generate continuity between external pieces.

The objective of the finger exotendon elastic structures or elastic elements (10) is to generate an elastic force towards finger extension and to restrict hand and finger flexing in typing positions and in positions where work is done on personal computers, or PCs, where the finger exotendon elastic structures are guided along a specific path of each tendon of the common extensor of the fingers by means of rigid guides (18) having two rigid guide side tabs (19) guiding the path of the elastic elements (10) over the metacarpals and the proximal phalanges of the hand and thumb, where the modular design allows replacement of these elastic elements (10) so as to customize them, adjust the tension, or perform maintenance.

The palm comprises external cushioned elements or pads disposed in anatomical positions for the purpose of releasing loads from areas where tendons, muscles, and nerves are located. The pads of the radial area (21) and the pads of the ulnar area (22) are disposed with a separation between them to favor loading on areas of the path of the radius and of the ulna, together with pads in the thenar area (24), the hypothenar area (25), and on the area of the palmar digital protuberance (25), being disposed to release pressure loading on the path of the carpal tunnel and hollow center of the palm where the main flexor tendons are located and to favor ventilation.

LIST OF PARTS

1 elasticated glove
2 finger securing area
3 wrist
4 rigid finger terminals
5 wrist securing area
6 certain height
Z finger connection bosses
8 elastic perforations
9 side tabs
10 elastic elements
11 connection terminal
12 extruded elastic bosses
13 central piece
14 central piece perforations
15 joining piece or wrist terminal
16 male articulation piece
17 female articulation piece
18 rigid guides
19 rigid guide side tabs
20 slots
21 cushioned elements in the radial area of the hand
22 cushioned elements in the ulnar area
23 cushioned elements in the hypothenar area
24 cushioned elements in the thenar area
25 cushioned elements in the palmar digital protuberance area

The invention claimed is:

1. An elasticized glove configured to fit over a patient's hand and extend to said patient's wrist for offloading extensor muscles and tendons of the patient's hand and preventing muscle and tendon pathologies in the patient's hand, the elasticized glove comprising:

an elasticized silicone layer at least at the glove's finger end and wrist distal end with the glove having an inside layer of silicone fabric;

a wrist terminal in a wrist securing area;

a central piece on the glove located in an area proximal to the dorsal carpus bones of the patient's hand, when arranged over the patient's hand, which joins with said wrist terminal by an articulation, said central piece defining a plurality of slots each with at least two central perforations;

a plurality of rigid finger terminals, each rigid finger terminal being defined on a finger securing element on each finger of the glove in an area proximal to a dorsal part of a medial phalange of a finger of the patient's hand, when arranged over the patient's hand, each securing element having two finger connection bosses;

at least four rigid guides on the glove located between the area proximal to the dorsal carpus bones of the patient's hand, when arranged over the patient's hand, and a knuckle area of the patient's hand, when arranged over the patient's hand, and four rigid guide pieces in the knuckle area of the patient's hand, when arranged over the patient's hand, with each rigid guide piece following the direction of a finger of the patient's hand when arranged over the patient's hand;

five elastic elements, one for each finger of the glove, comprising at one end two extruded elastic bosses, each of the elastic bosses being connectable to said central perforations, and at an other end, elastic perforations, complementary with said finger connection bosses of a rigid finger terminal, thereby defining different tension graduation levels according to a position in which the elastic elements are coupled, said elastic elements being located between said central piece and said rigid finger terminal, secured by said bosses and perforations, guided by rigid guides of the at least four rigid guides, and extending along a path of the extensor tendons of the fingers of the patient's hand, when arranged over the patient's hand, disposed in the paths extending from said central piece to the finger terminals to ensure the correct alignment thereof, with the elastic element which corresponds to the thumb of the glove being connected only between said central piece and said rigid finger terminal; and a plurality of pads disposed on a palm portion of the glove alignable with the palm of the hand in the radial area of the patient's hand, when arranged over the patient's hand, and, the ulnar area, the hypothenar area, the thenar area, and the area of the palmar digital protuberance.

2. The elasticized glove of claim 1, further comprising breathable, hypoallergenic, elastane, non-toxic, washable, anti-fungal silicone microfibers at least at the glove's finger end and the wrist distal end.

3. The elasticized glove of claim 2, wherein a distance from a securing point with terminals of said wrist securing area to said central piece is selected so as to eliminate friction between said elastic elements and any textile material in said glove.

4. The elasticized glove of claim 1, further comprising, at least in part, thermoplastic material.

5. The elasticized glove of claim 1, wherein any said rigid finger terminals comprises two side tabs for centering said elastic element.

6. The elasticized glove of claim 1, wherein said articulation comprises a male articulation piece with a shape extending onto a female articulation piece.

* * * * *